(12) United States Patent
van den Brink et al.

(10) Patent No.: US 7,531,139 B2
(45) Date of Patent: *May 12, 2009

(54) SYSTEM FOR PERFORMING EXPERIMENTS, IN PARTICULAR FOR HIGH THROUGHPUT EXPERIMENTATION

(75) Inventors: Peter John van den Brink, Driebergen (NL); Maarten Bracht, Amsterdam (NL); Bashir Husein Harji, Cottenham (GB)

(73) Assignee: Avantium International B.V., Amsterdam (NL)

( * ) Notice: Subject to any disclaimer, the term of this patent is extended or adjusted under 35 U.S.C. 154(b) by 897 days.

This patent is subject to a terminal disclaimer.

(21) Appl. No.: 10/703,390

(22) Filed: Nov. 7, 2003

(65) Prior Publication Data
US 2004/0115100 A1    Jun. 17, 2004

Related U.S. Application Data

(63) Continuation-in-part of application No. PCT/EP02/05321, filed on May 13, 2002.

(60) Provisional application No. 60/290,031, filed on May 11, 2001.

(30) Foreign Application Priority Data
May 11, 2001    (EP)    .................................. 01201739

(51) Int. Cl.
B01L 3/00    (2006.01)
(52) U.S. Cl. ...................................... 422/102; 422/104

(58) Field of Classification Search ................. 422/100, 422/102, 104
See application file for complete search history.

(56) References Cited

U.S. PATENT DOCUMENTS

| 4,787,988 A | 11/1988 | Bertoncini et al. |
| 5,709,840 A * | 1/1998 | Juranas ........................ 422/99 |
| 5,714,127 A | 2/1998 | DeWitt et al. |
| 5,866,342 A | 2/1999 | Antonenko et al. |

FOREIGN PATENT DOCUMENTS

| EP | 1 108 467 A2 | 6/2001 |
| WO | WO 97/09353 | 3/1997 |

\* cited by examiner

*Primary Examiner*—Jill Warden
*Assistant Examiner*—Natalia Levkovich
(74) *Attorney, Agent, or Firm*—Hoffmann & Baron, LLP

(57) ABSTRACT

The system comprises a tubular vessel allowing a flow of fluid through said vessel and an assembly for housing said vessel. The assembly comprises a base block having a first channel formed therein for removably housing the vessel, said first channel having first and second channel openings allowing introduction and/or discharge of a fluid into and from said first channel. The assembly also comprises a cover element having a bottom surface being releasably attachable to the first face of the base block. A first sealing element is provided between the first face of the base block and the bottom surface of the cover element, the first sealing element surrounding the first channel opening completely, and thereby sealing gastight around said first channel opening between the cover element and the base block. The system further comprises a second sealing element located in the first channel, said second sealing element sealing gastight against the inside of the first channel and the outside of the vessel.

14 Claims, 3 Drawing Sheets

SYSTEM FOR PERFORMING EXPERIMENTS, IN PARTICULAR FOR HIGH THROUGHPUT EXPERIMENTATION

CROSS-REFERENCE TO RELATED APPLICATIONS

This application is a continuation-in-part of International Application No. PCT/EP02/05321, filed May 13, 2002, which designated the U.S. and which claims the benefit of both Provisional Application No. 60/290,031, filed May 11, 2001, and European Application No. 01201739.8, filed May 11, 2001, the contents of which are incorporated by reference herein.

FIELD OF THE INVENTION

The present invention relates to a system for performing experiments, in particular for high throughput experimentation.

BACKGROUND OF THE INVENTION

Systems for high throughput experimentation ("HTE") are known and are used for simultaneously conducting a large number of experiments using a plurality of vessels, optionally with different reaction conditions. High throughput experimentation is used for instance in the pharmaceutical industry for the discovery and development of new and useful drugs and in the field of catalysts for the development of new catalysts (see e.g. Angew. Chem. Int. Ed. 1999, 38, No. 18, pp 2794-2803).

OBJECT OF THE INVENTION

The object of the invention is to provide an improved system.

SUMMARY OF THE INVENTION

The invention provides a system for performing experiments, in particular for high throughput experimentation. The system has at least one tubular vessel having a first vessel opening and a second vessel opening at opposite ends thereof allowing a flow of fluid through said vessel.

The system further includes an assembly for housing said vessel. This assembly has a base block having at least one first channel formed therein for removably housing the vessel, said first channel having a wall, a first channel opening, opening in a first face of the base block, and a second channel opening, opening in a second face of the base block, said first and second channel openings allowing introduction and/or discharge of a fluid into and from said first channel.

The assembly further includes a cover element having a bottom surface, the cover element with the bottom surface facing the base block being releasably attachable to the first face of the base block.

A first sealing element is present between the first face of the base block and the bottom surface of the cover element, the first sealing element surrounding the first channel opening completely, and thereby sealing gastight around said first channel opening between the cover element and the base block.

The tubular vessel and the first channel are such that an annular gap is present between the outside of the vessel and the wall of the first channel.

A second sealing element is located in the first channel, said second sealing element sealing gastight against the wall of the first channel and the outside of the vessel thereby sealing said annular gap.

A fourth channel is provided in the base block, which fourth channel opens into the gap between the second sealing element and the second channel opening.

Preferably the gap is between 0.01 and 1 millimeters, more preferably between 0.02 and 0.5 millimeters, most preferably between 0.05 and 0.2 millimeters.

In this system a flow of fluid from one end of the first channel to the other end has to pass through the tubular vessel as the second sealing element prevents a bypass flow between these ends along the outside of the vessel.

It will be understood that multiple second sealing elements can be provided along a part of the length of the vessel, e.g., a cluster of adjacent second sealing elements.

The second sealing element(s) can be fitted on the vessel or in the base block, or form part of a separate fitting to be mounted between the vessel and the inside of the first channel.

Preferably an annular gap is present between (a part of) the outside of the vessel and the inside of the first channel. The second sealing element(s) shuts off this gap at the location of said second sealing element.

The presence of an annular gap has multiple advantages. For instance the gap allows for diametrical expansion of the vessel (e.g. thermal expansion) without the vessel become stuck in the first channel. Also the annular gap prevents the vessel to become stuck in the first channel due to corrosion or intrusion of particles between the vessel and the inside of the first channel.

Also the gap allows for a fluid flow along parts of the length of the vessel between the second sealing element and one or both ends of the vessel as will be explained further below.

The first channels of the system according to the present invention are described herein as having first and second openings, opening in certain faces of the base block. The person skilled in the art will readily understand that these first and second openings may be inlets or outlets, depending on in which direction a fluid to be used flows. Usually, the first openings are inlets and the second openings outlets. For simplicity reasons, the first openings and second openings will be denoted as inlets and outlets respectively, throughout the description.

Furthermore, the person skilled in the art will readily understand that the first face and second face of the base block can be one and the same, i.e. the through going first channel may have both its inlet and outlet in the first face of the base block.

The first and second sealing elements used in the system according to the present invention may be O-rings. Such O-rings are not limited to a substantially circular cross-sectional form, but can have any suitable form for sealing, as will be well understood by a person skilled in the art. Further, the O-rings can be made from any suitable material, such as metal or an elastomer. Instead of O-rings, the sealing elements may have any other suitable form known to the person skilled in the art. For example, multiple layers of tape or V-shaped metal rings may also be used.

It is also envisaged that the first and second sealing elements form part of a unitary sealing structure, e.g. an O-ring positioned such that it effects both sealing functions.

According to a preferred embodiment of the system according to the present invention, the first sealing element is made from a high pressure resistant material, while the second sealing element is made from a resilient material such as for example rubber. Hereby, a very easy and gastight sealing can be obtained.

The selection of material of the sealing elements also depends on the temperatures present in the system, in particular of the base block. Usually, the temperature nearby the first face of the base block has a value allowing the sealing elements to be made from a resilient, elastomeric material.

The first and second faces of the base block and the bottom surface of the cover element may have any suitable form, as long as, in attached condition of the base block and cover element, a sufficient sealing of the vessels is obtained.

According to a preferred embodiment of the system according to the invention, both or any of the first face of the base block and the bottom surface of the cover element are substantially planar. Hereby, a very easy and very effective gastight sealing of the vessels can be obtained.

As mentioned above and as will be illustrated more clearly in the drawings hereinafter, the second sealing element is located in the first channel of the base block and around the vessel placed in the base block. According to a preferred embodiment of the present invention, the second sealing element is located in the vicinity of the first face of the base block. Hereby it is ensured that the fluid, which is fed into the inlet of the vessel, will be maintained under substantially the same conditions. Furthermore, the occurrence of dead volume can be avoided.

According to an advantageous embodiment, the base block comprises at least one second channel connecting to the first channel of the base block between the second sealing element and the first channel opening. Hereby a fluid can be easily fed to (or removed from) the first channel opening.

It is preferred that the cover element comprises at least one third channel in fluid communication with the at least one first channel in the base block. Hereby feeding of the individual vessels can be provided for, while the contents of the individual vessels are isolated from the contents of any other vessel contained in the base block.

Further it is preferred that the base block comprises a fourth channel opening into the first channel of the base block between the second sealing element and the second channel opening. Hereby a fourth channel can be brought in fluid communication with the second vessel opening.

The fourth channel can be used for purging purpose when said channel is connected to a supply of purging fluid. For example the fourth or purging channel can be brought in fluid communication with a pressurised source of an inert fluid such as $N_2$. Hereby for example a product gas obtained by treatment in the vessel can be prevented from condensing by diluting said product gas by use of the inert fluid. Furthermore, the treatment process using the system as a whole can be accelerated as the product gas is more efficiently obtained.

Using a preferred embodiment of the system according to the present invention a plurality of vessels housed in a base block can be sealed simultaneously and in a very easy manner by attaching the cover element to the base block housing the vessels, whereby all vessels are sealed in a gastight manner.

The person skilled in the art will readily understand that further feeding channels, sealing elements, etc. may be provided.

Finally, the present invention relates to methods for operating the system according to the present invention.

Hereinafter, the present invention will be illustrated in more detail by a drawing.

DETAILED DESCRIPTION OF PREFERRED EMBODIMENTS

Figure 1:
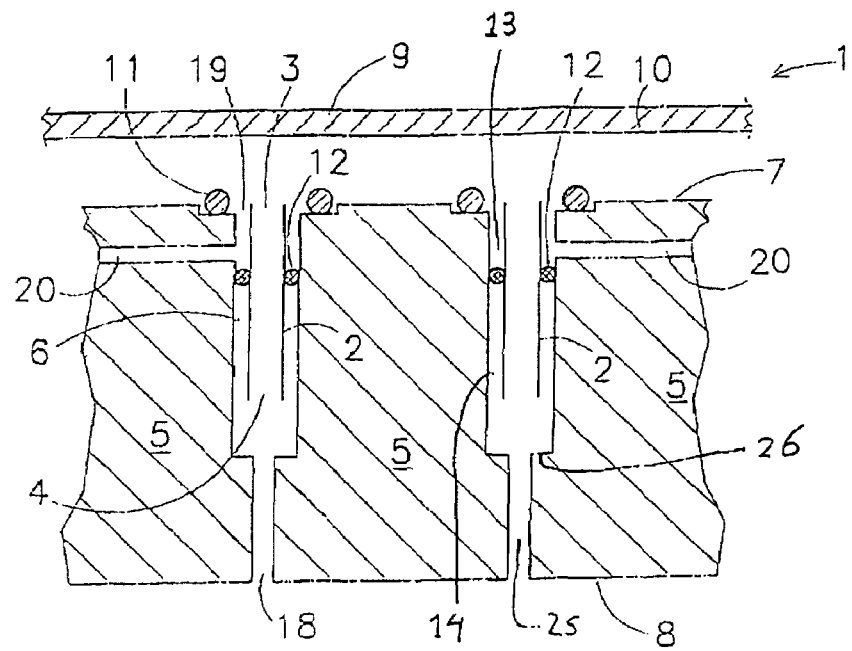
FIG. 1 shows a schematic cross-sectional view of a system according to the present invention in a partly assembled state.

In FIG. 1 a schematic cross-sectional view of a system according to the present invention is shown in partly assembled state. The system comprises an assembly 1 for housing a plurality of tubular vessels 2 of rectinilear shape having a first vessel opening (inlet 3) and a second vessel opening (outlet 4) at the opposite ends thereof. The vessels 2 may be embodied as tubes of metal or other suitable material.

The assembly 1 comprises a base block 5 and a cover element 9. The base block 5 has a plurality of through going first channels 6 formed therein for removably housing the vessels 2.

The first channels 6 each have a first channel opening (inlet 19), opening in a first face 7 of the block 5 and a second channel opening (outlet 18), opening in a second face 8 of the block 5.

The first channels 6 are formed here as bores in the solid base block 5. However other designs, wherein a first channel 6 is entirely or partly formed by a tubular part of the base block 5 are also possible.

The vessels 2 have a length such that each vessel 2 is entirely accommodated within the first channel 6.

In FIG. 1 it can be seen that an extension channel 25 is formed extending coaxially and in line with the first channel 6. The extension channel 25 extends between the lower end of the first channel and the second face 8 of the base block 5. The extension channel 25 has a smaller diameter than the first channel 6, so that an annular shoulder 26 is formed.

The vessel 2 can be designed to rest upon this annular shoulder 26.

In a variant not shown here, both the inlet 19 and the outlet 18 may open into the first face 7 of the block 5.

In the embodiment of FIG. 1 the first face 7 of the base block 5 is facing towards the cover element 9. The cover element 9 is releasably attachable on the first face 7 of the base block 5. There may be fastening means provided, such as screws, to attach the cover element 9 to the base block 5.

Between the first face 7 of the base block 5 and the bottom surface 10 of the cover element 9, a number of high pressure resistant O-rings 11 are provided as first sealing elements. These O-rings 11 are placed such that the O-ring 11 is near the inlet 19 of the first channel 6 and surrounds this inlet 19. Hereby leakage between neighbouring first channels 6 is prevented.

As is shown, annular grooves are provided in the first face 7 of block 5 for receiving the O-ring 11. This also prevents movement of the O-rings 11 in case of a horizontal movement of the cover element 9. Alternatively, the annular grooves may be provided in the bottom surface 10 of the cover element 9.

The assembly 1 is further provided with resilient O-rings 12 acting as second sealing elements. These O-rings 12 are located in the first channels 6 of the base block 5.

Figure 4:
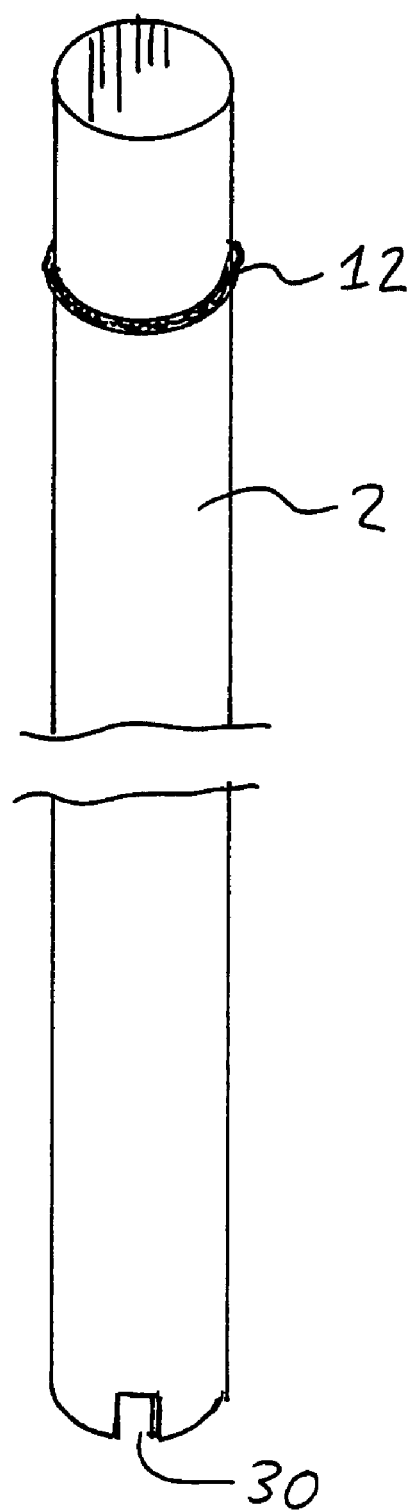
FIG. 4 shows a perpective view of a vessel.

In FIG. 4 it can be seen that the O-ring 12 is mounted on the outside of the tubular vessel 2, preferably located in a circumferential groove in the vessel 2. The second sealing element 12 could also be integral with the wall of the vessel 2, such as a thin flexible annular lip extending around the circumference of the vessel.

As the diameter of the vessel 2 is less than the diameter of the first channel 6 an annular gap is present between the outside of the vessel 2 and the wall of the first channel 6. The O-ring 12 is placed such that this annular gap is divided into two zones 13, 14. These two zones 13, 14 in the first channel 6 are sealed from each other in a gastight manner by the sealing element 12 between them. Of course, fluid communication may take place between zone 13 and 14 via the vessel 2.

In a preferred embodiment the vessel 2 has at the side of the second opening 4 side openings 30 (see FIG. 4) to allow fluid flow via the gap located below the second sealing element 12.

In the embodiment of FIG. 1, an easy and simultaneously sealing of the first channels 6 of the system can be obtained by attaching the cover element 9 to the base block 5.

The first and second sealing elements 11, 12 may have any suitable form, as long as a sufficient sealing is obtained. For example the first sealing element 11 may be made of a high pressure resilient (and, if desired, heat resistant) material such as a rubber, but may also be made of the same material as the base block 5 and cover element 9 (preferably a metal). The person skilled in the art will understand that the sealing element 11 may form part of the base block 5 or the cover element 9.

The second sealing element 12 is preferably made of a resilient material, for example an elastomeric material such as for instance rubber.

In FIG. 1 the cover element 9 is closed and has no internal channels connecting to the first channels 6. This allows the cover element 9 to be designed as a simple plate element.

In FIG. 1 additional second channels 20 are provided in the base block 5 for fluid communication with the inlet 3 of the vessels 2. These second channels 20 each connect to a first channel 6 between the second sealing element 12 and the first opening 19 of the first channel 6.

Figure 2:
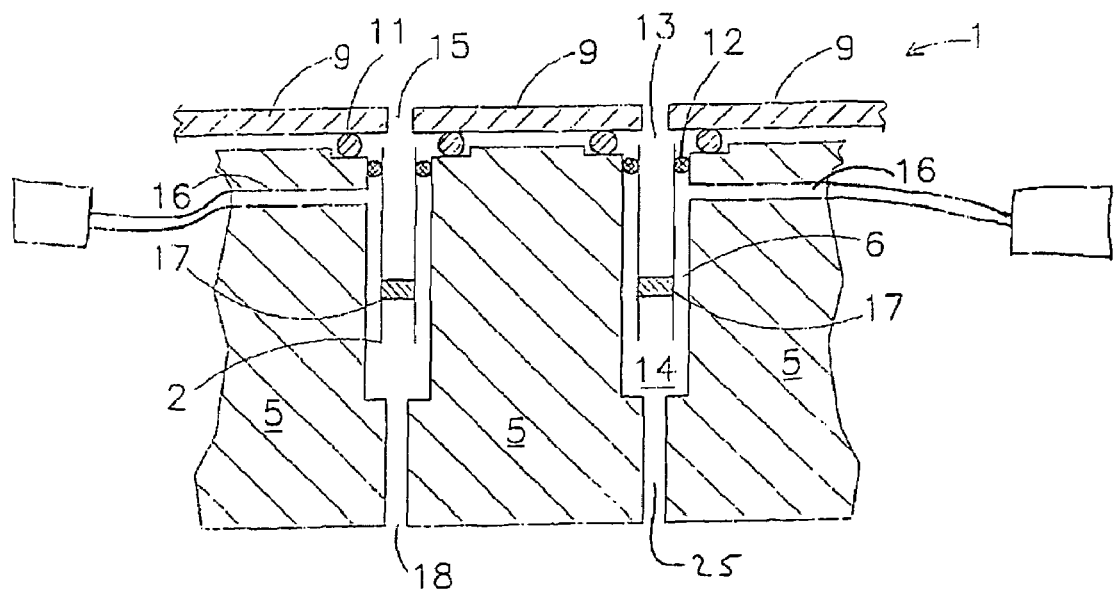
FIG. 2 shows a schematic cross-sectional view of an alternative system according to the present invention in assembled state.

FIG. 2 shows a schematic cross-sectional view of an alternative embodiment of the system shown in FIG. 1, in assembled state of the cover element 9 and the base block 5. Parts corresponding to the system of FIG. 1 have the same reference numerals.

The cover element 9 is provided here with third channels 15 each connecting to the inlet 3 of a vessel 2.

The vessels 2 each contain a reaction zone 17, for example containing a catalyst in the form of a catalyst bed.

The base block 5 according to the embodiment shown in FIG. 2 comprises fourth channels 16 opening into zone 14, i.e. the space in first channel 6 outside the vessel 2 and below the second sealing element 12.

The fourth channels 16 can be used for example for purging or diluting purposes. For example the fourth channel 16 may be in fluid communication with a pressurised source of an inert fluid such as $N_2$.

To prevent condensing of the product obtained in the reactor zone 17, if a gaseous product is obtained, an inert gas such as $N_2$ can be fed by fourth channel 16 to force the product obtained in the experiment through the outlet 18 of first channel 6. Herewith a very easy diluting of the product gas can be obtained and condensing can be prevented.

In a possible application of the system of FIG. 2, a fluid to be treated is fed via third channel 15 to the inlet 3 of the vessel 2. This third channel 15 will of course usually be provided with further sealing means or valves to prevent the fed fluid from returning to the third channel 15. After passing the reactor zone 17 the treated fluid will enter the zone 14 and be discharged via outlet 18.

In practice second channels 20 are preferably used for feeding gaseous products whereas third channels 15 are preferably used for feeding liquid products. For the feeding of a liquid for instance a capillary may be used, which may be partially inserted in the third channel 15.

It will be apparent that the second and third channels 20 and 15 can also be used for discharging product, which has passed through a vessel 2.

Figure 3:
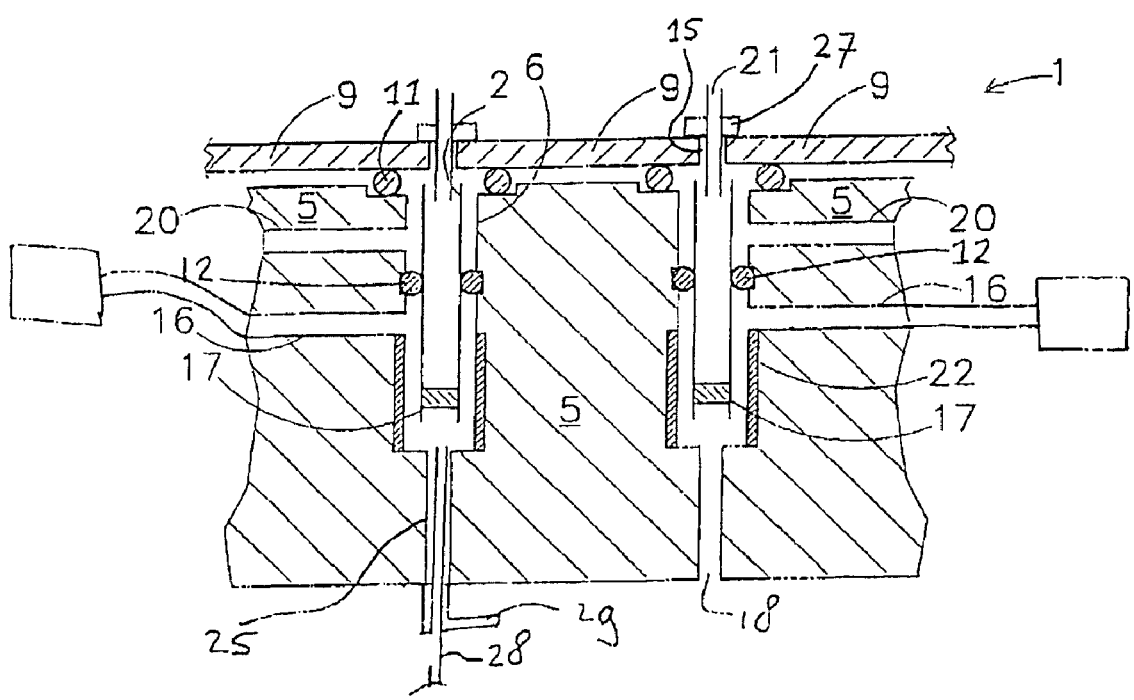
FIG. 3 shows a schematic cross-sectional view of a further alternative system according to the present invention in assembled state.

FIG. 3 shows a schematic cross-sectional view of a further alternative embodiment of the system according to the present invention.

The base block 5 has fourth channels 16, e.g. for purging purposes, and second channels 20, e.g. for feeding a fluid to the inlet 3 of the vessel 2.

In this embodiment the sealing elements 12 are located between the mouth of the second and fourth channels 20 and 16 respectively.

A sealing element 12 is placed in an annular groove in the wall of the first channel 6 to prevent movement of the sealing element 12 when the vessel 2 is inserted or removed or under the influence of a pressure difference.

Furthermore, the assembly 1 in FIG. 3 has a fluid feed conduit 21 extending through a third channel 15 in the cover 9, such as a capillary, e.g. for feeding a liquid in the inlet 3 of the vessel 2. A sealing means 27 is provided here for sealing the passage of the conduit 21 through the cover element 9.

The assembly of FIG. 3 furthermore shows the possibility to arrange a second fluid conduit 28 such that it extends into the extension channel 25. The diluted reaction product can be removed via fourth channel 16 or via the now annular extension channel 25 connecting to outlet 29.

Otherwise a fourth sealing means could be provided to seal the annular gap between the second fluid conduit 28 and the base block 5.

The second fluid conduit 28 could be designed as a capillary, e.g. for feeding a (diluting) fluid into the space below the vessel 2.

The second fluid conduit 28 could e.g. also be used for removing a sample of reaction product from the first channel 6. If the fluid flow through the vessel 2 were to be inversed the first fluid conduit 21 could be used for the same purposes.

The wall of the first channel 6 is provided with heating means 22 for locally heating the vessel 2, in this embodiment in particular the reactor zone 17.

In the embodiment shown in FIG. 3, the reactor block 5 provides for such a heating that only the reactor zone 17 will be significantly heated, while other parts of the assembly may be maintained at a lower temperature.

Preferably the heating means 22 are designed such that the sealing elements 12 are allowed to be made from an elastomeric material, without being degraded by the heat generated by the heating means 22.

The person skilled in the art will understand that many modifications can be made. For instance, the assembly 1 may be provided with further heating means for obtaining a specific temperature in certain parts of the block 5. Also, flow rate regulating elements, such as capillaries may be incorporated in the vessels 2. Further, the person skilled in the art will understand that the invention is not limited to an embodiment wherein the cover element 9 lies upon the base block 5; the assembly 1 may also be configured such that the cover element 9 is positioned under or next to the base block 5. Further, the first channels 6 in the base block 5 may be in the form an array, i.e. comprising several rows of parallel first channels 6.

It will be apparent as an alternative to heating means or in combination therewith cooling means can be provided in order to cool (a part of) the vessel 2 and/or base block 5. In a preferred embodiment a cooling means is provided in the region of the inlet of the vessel, e.g. to prevent liquid entering the vessel from boiling at this location.

As will be clear from the above, the system according to the present invention provides for a very easy and simultaneous sealing of at least one, but usually pluralities of vessels.

As is mentioned above, openings described as "inlet" may also function as outlet, depending on the flow direction of the fluid. This also applies for "outlet" which may, when desired and appropriate, function as inlet.

What is claimed is:

1. A system for performing experiments, in particular for high throughput experimentation, said system comprising:
    at least one tubular vessel, said vessel having a first vessel opening and a second vessel opening at opposite ends thereof allowing a flow of fluid through said vessel,
    an assembly for housing said vessel, said assembly comprising:
        a base block having a first face, a second face, and a first channel formed in said base block,
        said first channel having a wall, a first opening, and a second opening, said first opening of said first channel extends through said first face of the base block, and said second opening of the first channel extends through said second face of the base block, said first and second openings of the first channel allowing introduction and/or discharge of a fluid into and from said first channel,
        a cover element having a bottom surface, the bottom surface extending over said first face of the base block and over the first opening of the first channel, said bottom surface arranged adjacent and parallel to the first face of the base block;
        a first sealing element arranged between the first face of the base block and the bottom surface of the cover element, the first sealing element surrounding the first opening of the first channel completely, and thereby sealing gastight around said first opening of the first channel between the cover element and the base block;
    the wall of the first channel, the first sealing element, the bottom surface of the cover element and the second opening of the first channel together delimiting a cavity, said tubular vessel being entirely accommodated in said cavity in such a way that an annular gap is present between the tubular vessel and the wall of the first channel,
        in which system a second sealing element is located in the first channel, said second sealing element sealing gastight against the vessel and the wall-of the first channel, thereby sealing said annular gap; and
        a fourth channel is provided in the base block, said fourth channel opens into the annular gap between the second sealing element and the second vessel opening, and
        a feed channel for feeding fluid into the cavity, which feed channel is in fluid communication with the cavity, the feed channel being fluid communication with the second opening of the first channel via the tubular vessel.

2. A system according to claim 1, wherein said gap is between 0.01 and 1 millimetres.

3. A system according to claim 1, wherein the second sealing element is located in the vicinity of the first face of the base block.

4. A system according to claim 1, wherein the base block comprises a second channel connecting to the first channel between the second sealing element and the first opening.

5. A system according to claim 1, wherein the cover element comprises a third channel in fluid communication with the at least one first channel in the base block.

6. A system according to claim 1, wherein the vessel contains a reaction zone.

7. A system according to claim 1, wherein heat exchange means are provided for controlling the temperature of a part of the vessel.

8. A system according to claim 1, wherein said base block has multiple first channels each housing a tubular vessel.

9. A system according to claim 1, wherein said base block has multiple first channels each housing a tubular vessel, and wherein a single cover element covers the first face of the base block and thereby the first openings of all first channels.

10. A system according to claim 1, wherein the system comprises a means for feeding a fluid via said fourth channel into the gap.

11. A system according to claim 1, wherein the first face of the base block is opposite from the second face, and wherein the second opening is formed by an extension channel, extending in line with said first channel and opening into said second face.

12. A system according to claim 1, wherein the cover element comprises a third channel, in fluid communication with the at least one first channel in the base block, and wherein a first fluid conduit extends through said third channel and is in communication with said first opening.

13. A system according to claim 1, wherein the first face of the base block is opposite from the second face, and wherein the second opening is formed by an extension channel, extending in line with said first channel and opening into said second face, and wherein a second fluid conduit extends through said extension channel and is in communication with said second opening.

14. A system for performing experiments, in particular for high throughput experimentation, said system comprising:
    at least one tubular vessel, said vessel having a first vessel opening and a second vessel opening at opposite ends thereof allowing a flow of fluid through said vessel; and
    an assembly for housing said vessel, said assembly comprising:
    a base block having a first face, a second face, and a first channel formed in said base block,
    said first channel having a wall, a first opening, and a second opening, said first opening of said first channel extends through said first face of the base block, and said second opening of the first channel extends through said second face of the base block, said first and second openings of the first channel allowing introduction and/or discharge of a fluid into and from said first channel,
    a cover element having a bottom surface, the bottom surface extending over said first face of the base block and over the first opening of the first channel, said bottom surface arranged adjacent and parallel to the first face of the base block;

a first sealing element is located in the first channel, said first sealing element sealing gastight against the vessel and the wall-of the first channel, thereby sealing said annular gap; and the wall of the first channel, the first sealing element, the bottom surface of the cover element and the second opening of the first channel together delimiting a cavity, said tubular vessel being entirely accommodated in said cavity in such a way that an annular gap is present between the tubular vessel and the wall of the first channel;

a fourth channel is provided in the base block, said fourth channel opens into the annular gap between the first sealing element and the second vessel opening; and a feed channel for feeding fluid into the cavity, which feed channel is in fluid communication with the cavity, the feed channel being fluid communication with the second opening of the first channel via the tubular vessel.

* * * * *